(12) United States Patent
Li et al.

(10) Patent No.: US 11,577,043 B2
(45) Date of Patent: Feb. 14, 2023

(54) BRAIN STIMULATION SYSTEM, METHOD AND APPARATUS BASED ON ARTIFICIAL INTELLIGENCE AND STORAGE MEDIUM

(71) Applicant: SHENZHEN INSTITUTES OF ADVANCED TECHNOLOGY, Nanshan Shenzhen (CN)

(72) Inventors: Xiaotao Li, Nanshan Shenzhen (CN); Juan Li, Nanshen Shenzhen (CN); Haiyang Yang, Shenzhen (CN); Liping Wang, Shenzhen (CN)

(73) Assignee: SHENZHEN INSTITUTES OF ADVANCED TECHNOLOGY, Guangdong (CN)

( * ) Notice: Subject to any disclaimer, the term of this patent is extended or adjusted under 35 U.S.C. 154(b) by 969 days.

(21) Appl. No.: 16/248,902

(22) Filed: Jan. 16, 2019

(65) Prior Publication Data
US 2019/0358425 A1  Nov. 28, 2019

(30) Foreign Application Priority Data
May 23, 2018  (CN) .......................... 201810500943.9

(51) Int. Cl.
*A61M 21/00* (2006.01)
*A61B 5/0533* (2021.01)
(Continued)

(52) U.S. Cl.
CPC ........... *A61M 21/00* (2013.01); *A61B 5/0077* (2013.01); *A61B 5/02416* (2013.01);
(Continued)

(58) Field of Classification Search
CPC .................. A61M 21/00; A61M 21/02; A61M 2021/0005; A61M 2021/0011;
(Continued)

(56) References Cited

U.S. PATENT DOCUMENTS

2011/0118555 A1* 5/2011 Dhumne ............... A61M 21/02
  600/300
2013/0281759 A1* 10/2013 Hagedorn .......... A61N 1/36025
  600/15

(Continued)

FOREIGN PATENT DOCUMENTS

CN  201060561  5/2008
CN  104573360  4/2015

(Continued)

*Primary Examiner* — Carrie R Dorna
(74) *Attorney, Agent, or Firm* — Woodard, Emhardt, Henry, Reeves & Wagner, LLP

(57) ABSTRACT

Provided are a brain stimulation system, method, apparatus and storage medium based on artificial intelligence. The system includes: a plurality of brain stimulation terminals and a cloud platform. The cloud platform is configured to, with artificial intelligence algorithm especially machine learning and deep learning, generate multi-dimensional psychological big data using physiological data and psychological state evaluation parameters gotten from the plurality of brain stimulation terminals and established models of algorithm for disease diagnosis. The brain stimulation terminal is configured to analyze the physiological data and psychological state evaluation parameters of a target subject, measure a mental state of the target subject, obtain brain stimulation parameters required for the target subject according to the mental state, and generate corresponding non-invasive brain stimulation for the target subject according to the brain stimulation parameters based on the multi-dimensional big data through the artificial intelligence algorithm.

21 Claims, 9 Drawing Sheets

(51) Int. Cl.
  *A61B 5/024* (2006.01)
  *A61B 5/00* (2006.01)
  *A61N 5/06* (2006.01)
  *A61N 7/00* (2006.01)
  *A61B 5/16* (2006.01)
  *A61B 5/369* (2021.01)

(52) U.S. Cl.
  CPC ............ *A61B 5/0533* (2013.01); *A61B 5/165* (2013.01); *A61B 5/369* (2021.01); *A61N 5/0618* (2013.01); *A61N 7/00* (2013.01); *A61M 2021/0016* (2013.01); *A61M 2021/0022* (2013.01); *A61M 2021/0027* (2013.01); *A61M 2021/0055* (2013.01); *A61M 2205/058* (2013.01); *A61M 2205/3303* (2013.01); *A61M 2205/3327* (2013.01); *A61M 2210/0693* (2013.01); *A61N 2007/0026* (2013.01)

(58) Field of Classification Search
  CPC .. A61M 2021/0016; A61M 2021/0022; A61M 2021/0027; A61M 2021/0038; A61M 2021/0044; A61M 2021/005; A61M 2021/0055; A61B 5/02416; A61B 5/0077; A61B 5/0533; A61B 5/0618; A61B 5/165; A61B 2205/058; A61B 2205/3303; A61B 2205/3327
  See application file for complete search history.

(56) References Cited

U.S. PATENT DOCUMENTS

2014/0347265 A1* 11/2014 Aimone ................ A61B 5/163
                                                    345/156
2015/0105837 A1*  4/2015 Aguilar Domingo . A61B 5/374
                                                    607/45

FOREIGN PATENT DOCUMENTS

| CN | 105078449 | 11/2015 |
| CN | 106280044 | 1/2016  |
| CN | 105816170 | 8/2016  |
| CN | 107402635 | 11/2017 |
| CN | 107799165 | 3/2018  |
| CN | 207217123 | 4/2018  |

* cited by examiner

BRAIN STIMULATION SYSTEM, METHOD AND APPARATUS BASED ON ARTIFICIAL INTELLIGENCE AND STORAGE MEDIUM

CROSS-REFERENCES TO RELATED APPLICATIONS

This application claims priority to a Chinese patent application No. 201810500943.9 filed on May 23, 2018, disclosure of which is incorporated herein by reference in its entirety.

TECHNICAL FIELD

Embodiments of the present disclosure relate to medical appliances and the intelligent product technology and, in particular, to a brain stimulation system, method and apparatus based on artificial intelligence, and storage medium.

BACKGROUND

Psychological research shows that the majority of people encounter different levels of psychological disorders or mental illnesses at different life stages. Especially in the digital era with mass information, faced with pressure from work and life, people often feel nervous, anxious and depressed. Many people are in the sub-health state that they are physically and mentally exhausted, which leads to an increase in factors that endanger mental health. In recent years, the incidence of serious mental illnesses such as depression, autism, and schizophrenia in the society is increasing. In addition, with the aging of global population, an increasing number of people suffer from neurodegenerative diseases including Alzheimer's disease and Parkinson's disease. These various brain diseases related to the nervous system bring an increasingly heavy burden to families and the society in addition to causing great pain to patients.

Now there is a lack of highly effective treatments for these brain diseases. Traditionally, the drug therapy is employed. However, a significant breakthrough has not been made in drug research based on medicinal chemistry and genetics, a drug that is effective and safe in the long term is difficult to find, and these research incur huge costs. Surgical treatment is also employed for some major neurological diseases, but, due to a limited knowledge of the complexity of the brain and the nervous system, any carelessness during surgical treatment tends to cause unpredictable consequence. In recent years, with the development of big data and artificial intelligence (AI) technology in healthcare system, human health issues may be treated from a new engineering perspective and better solutions may be found. Minimally invasive brain stimulation techniques have been used by far to treat brain diseases such as Parkinson's disease, depression and stroke. Mature minimally invasive brain stimulation techniques specifically include transcranial direct current stimulation (tDCS), deep brain stimulation (DBS) and repetitive transcranial magnetic stimulation (rTMS). In addition, currently AI used in a medical and health field is mainly focus on medical diagnosis. For example, Avalon AI detects functional magnetic resonance images of the brain with AI tech to predict the incidence of Alzheimer's disease. Cognoa has designed a set of AI software for early screening of child autism. And Embrace wristband from MIT media lab which was just approved by the US FDA in February 2018, is able to conduct early diagnosis to epileptic seizures.

However, the above-mentioned techniques and products have some disadvantages that limit their more applications.

In terms of minimally invasive brain stimulation techniques, the tDCS has a limited temporal-spatial resolution in the brain region due to the diffusion effect of an electric field. The DBS also has limitation despite there are some good effects. For example, the DBS has certain unpredictability and even side effects, because this stimulation is often lack of selectivity and specificity, and its treatment mechanism is unclear in many cases. Although optogenetic stimulation is proved to have unique advantage of neuronal specificity and selectivity in animal experiments, the long-term implantation of its stimulation device in the brain will cause an immunological rejection and inflammatory response just like the DBS, and then its stimulation effect is likely to gradually weaken. The magnetic field strength of the rTMS decays rapidly with an increase of the distance, and thus an induced current can substantially only act on the cerebral cortex. Although an ultrasound stimulation technique is almost non-invasive and the ultrasound wave probably penetrate into a deep brain region in the theory, the accuracy and intensity of that technique to stimulate a brain nucleus remain to be further improved (Landhuis E, Nature 2017). On the other hand, the application of the artificial intelligence algorithm in the medical field is still at an early developing stage and that is insufficiently mature. For example, although the Embrace wristband can monitor human physiological data at any time through skin contact, and predict epileptic seizures in time, now such products are only helpful for providing early diagnosis but without further intervention or treatment. The Woebot chat robot is a typical representative in treating mental illnesses by human-machine interaction, supported by many netizens, however, this simple cognitive behavioral therapy (CBT) has relatively modest effect on severe mental illnesses. Social robots such as KASPAR developed by the University of Hertfordshire in United Kingdom have certain effect on rehabilitation training for autistic children, but those products are relatively restricted in intelligent function artificial intelligence algorithm.

SUMMARY

Embodiments of the present disclosure provide an AI-based brain stimulation system, method, and apparatus as well as a storage medium, which are used for maintaining mental health and easing negative emotions for the ordinary people and providing at least early prediction, timely prevention and professional intervention for severe mental illnesses.

According to a first aspect, the embodiments of the present disclosure provide a brain simulation system based on artificial intelligence especially computer vision, natural language processing, machine learning and deep learning. The system includes: a plurality of brain stimulation terminals and a cloud platform in connection with the plurality of brain stimulation terminals.

The cloud platform is configured to, with artificial intelligence algorithm especially deep learning, generate multi-dimensional psychological big data using physiological data and psychological state evaluation parameters gotten from the plurality of brain stimulation terminals and established models of algorithm for disease diagnosis.

The brain stimulation terminal is configured to: analyze, with artificial intelligence algorithm, collected physiological data and psychological state evaluation parameters of a target subject based on the multi-dimensional psychological big data, measure a mental state of the target subject, obtain brain stimulation parameters required for the target subject according to the mental state, and produce a non-invasive brain stimulation for the target subject according to the brain stimulation parameters.

In an exemplary embodiment, the brain stimulation terminal includes a physiological information collection device, a psychological communication interaction device, a central control processing device and a physical output apparatus.

The physiological information collection device is configured to collect the physiological data of the target subject.

The psychological communication interaction device is configured to perform human-machine interaction with the target subject through a natural language processing technology and acquire the psychological state evaluation parameters of the target subject.

The central control processing device is configured to control the physiological information collection device, the psychological communication interaction device and the physical output apparatus, and to analyze the physiological data and psychological state evaluation parameters of the target subject based on the multi-dimensional psychological big data and by using the algorithm, measure a mental state of the target subject, and obtain the brain stimulation parameters required for the target subject according to the mental state.

the physical output apparatus is configured to operate according to the brain stimulation parameters to produce the brain stimulation for the target subject.

In an exemplary embodiment, the cloud platform is further configured to, through the artificial intelligence algorithm, perform cycled calculation on the multi-dimensional psychological big data and optimize the multi-dimensional psychological big data.

In an exemplary embodiment, the brain stimulation terminal is further configured to predict a possibility of a mental illness of the target subject according to the mental state and make corresponding pre-warnings and/or adjustment and intervention.

In an exemplary embodiment, the brain stimulation terminal is further configured to comprehensively record the brain stimulation parameters of the target subject, optimize the brain stimulation parameters of the target subject to obtain a brain stimulation rule suitable for the target subject through the artificial intelligence algorithm, and produce individual-targeted brain stimulation for the target subject according to the brain stimulation rule.

In an exemplary embodiment, the physiological information collection device is configured to collect the physiological data by sensors, where the sensors comprise a galvanic skin response collection device, a brain wave collection device and a photoelectric plethysmograph device.

In an exemplary embodiment, the physiological information collection device is further configured to collect facial expressions of the target subject through a camera and collect sound features of the target subject through a microphone.

The central control processing device is further configured to analyze the facial expressions and the sound features of the target subject through the artificial intelligence algorithm and measure the mental state of the target subject.

In an exemplary embodiment, the physical output apparatus includes one or more of the following devices: a light source device, a sound device, a massage device, an incense device, an ultrasonic device and an electromagnetic wave device.

In an exemplary embodiment, the light source device, the sound device and the massage device are configured to provide physical sensory stimulation for performing a stimulation program on the target subject.

In an exemplary embodiment, the incense device is configured to spread chemical gas molecules via air into an olfactory organ of the target subject to achieve an olfactory drug delivery intervention or treatment effect.

In an exemplary embodiment, the ultrasonic device and the electromagnetic wave device are configured to perform a professional brain stimulation on the target subject to achieve an intervention treatment effect in a specific brain region.

In an exemplary embodiment, the psychological communication interaction device is further configured to perform a cognitive behavior therapy on the target subject through the human-machine interaction with the target subject, wherein the human-machine interaction comprises written communication, voice conversation, game interaction, picture playback and/or video playback.

In an exemplary embodiment, the brain stimulation terminal further includes a power supply device configured to supply power to the brain stimulation terminal. The power supply device includes one or more of the following devices: a primary battery, a secondary battery, a radio frequency power supply battery, and a biofuel battery.

In an exemplary embodiment, the physiological data includes a heart rate, a respiratory rate, a blood pressure, skin conductivity and a brain wave, and the psychological state evaluation parameters comprise a pressure index, an attention value and a fatigue level.

According to a second aspect, the embodiments of the present disclosure provide an AI based brain stimulation method. The method includes:

collecting physiological data of a target subject, performing human-machine interaction with the target subject through a natural language processing technology, and acquiring psychological state evaluation parameters of the target subject;

based on multi-dimensional big data and by using artificial intelligence algorithm, analyzing the physiological data and the psychological state evaluation parameters, measuring a mental state of the target subject, and obtaining brain stimulation parameters required for the target subject according to the mental state; and producing a non-invasive brain stimulation for the target subject according to the brain stimulation parameters.

In an exemplary embodiment, the method further includes:

by using the artificial intelligence algorithm, generating the multi-dimensional big data by learning a plurality of physiological data and psychological state evaluation parameters and according to the established models of algorithm for disease diagnosis.

In an exemplary embodiment, the method further includes:

performing cycled calculation on the multi-dimensional big data through the artificial intelligence algorithm and optimizing the multi-dimensional big data.

In an exemplary embodiment, the method further includes:

predicting a possibility of a mental illness of the target subject according to the mental state and making corresponding pre-warnings and/or adjustment and intervention.

In an exemplary embodiment, the method further includes:

comprehensively recording the brain stimulation parameters of the target subject, optimizing the brain stimulation parameters of the target subject to precisely obtain a brain stimulation rule suitable for the target subject through the artificial intelligence algorithm, and producing individual-targeted brain stimulation for the target subject according to the brain stimulation rule.

In an exemplary embodiment, the method further includes:

collecting facial expressions of the target subject through a camera and collecting sound features of the target subject through a microphone, analyzing the facial expressions and the sound features of the target subject through the artificial intelligence algorithm and measuring the mental state of the target subject.

According to a third aspect, the embodiments of the present disclosure provide an apparatus including a memory, a processor, and programs stored in the memory and executable on the processor. When executing the programs, the processor implements the AI based brain stimulation method according to the second aspect.

In an exemplary embodiment, the apparatus includes any one of the following: a smartphone, a computer, an intelligent pet, and a smart medical instrument.

According to a fourth aspect, the embodiments of the present disclosure provide a storage medium including executable instructions. When executed by a processor, the executable instructions are configured to implement the AI based brain stimulation method according to the second aspect.

The embodiments of the present disclosure can provide accurate prediction, prevention and intervention for physical and mental health problems in an intelligent, individual-targeted, scientific and comprehensive manner. The embodiments of the present disclosure employ a mental health detection technology and provide individual-targeted, comprehensive, and scientific prevention and intervention after individual detection, including the cognitive behavioral therapy, the physical stimulation therapy and the olfactory drug delivery therapy. In addition, the embodiments have certain effects on a plurality of brain diseases in conjunction with big data and artificial intelligence, and particularly provide at least early prediction, timely prevention and professional intervention for depression, autism and schizophrenia. Besides the cognitive behavioral therapy through the human-machine interaction system, more comprehensive and complete prevention and intervention are implemented, including an accurate physiological and psychological monitoring system, a non-invasive multi-sensory brain stimulation technology and a seizure emergency alert function. Therefore, the embodiments can not only help people maintain mental health and regulate negative emotions, but also help to treat the most serious mental illnesses including depression, autism and schizophrenia.

DETAILED DESCRIPTION

Figure 1:
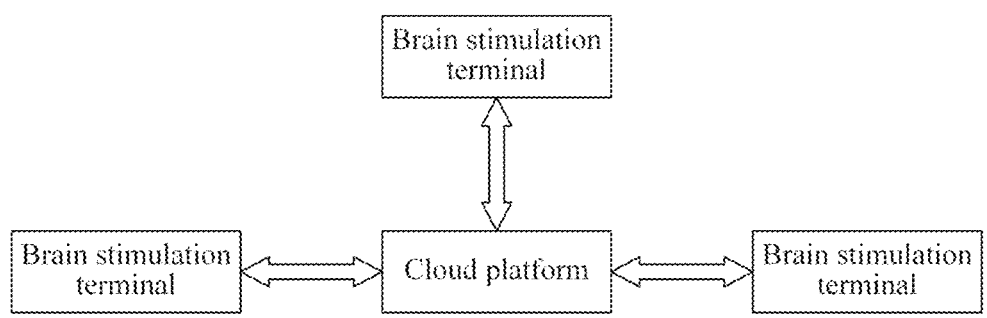
FIG. 1 is a block diagram illustrating a configuration of a brain stimulation system based on artificial intelligence according to embodiments of the present disclosure.

Hereinafter embodiments of the present disclosure will be described in detail with reference to the accompanying drawings. It should be understood that the specific embodiments are described herein merely to explain the embodiments of the present disclosure, and not to limit them. It is also to be noted that, for convenience of description, only some but not all structures related to the embodiments of the present disclosure are shown in the drawings.

FIG. 1 is a block diagram illustrating a configuration of a brain stimulation system based on artificial intelligence according to an embodiment of the present disclosure. Referring to FIG. 1, the system includes: a plurality of brain stimulation terminals and a cloud platform.

The plurality of brain stimulation terminals are communicatively connected to the cloud platform respectively. The cloud platform is used for generating, with artificial intelligence algorithm especially machine learning and deep learning, multi-dimensional psychological big data by using established models of algorithm for various disease diagnosis, and physiological data and psychological state evaluation parameters that are gotten from the plurality of brain stimulation terminals. The brain stimulation terminal is used for analyzing physiological data and psychological state evaluation parameters collected from a target subject through the artificial intelligence algorithm, measuring a mental state of the target subject, obtaining brain stimulation parameters required for the target subject according to the mental state, and generating a corresponding non-invasive brain stimulation for the target subject according to the brain stimulation parameters based on the multi-dimensional psychological big data.

On the basis of the above-mentioned technical solution, the cloud platform is also used for performing cycled calculation on the multi-dimensional psychological big data and optimizing the multi-dimensional psychological big data by means of the artificial intelligence algorithm. The brain stimulation terminal is further used for predicting the possibility of a mental illness of the target subject according to the mental state and providing corresponding pre-warnings and/or adjustment and intervention. The brain stimulation terminal is further used for comprehensively recording the brain stimulation parameters of the target subject, and optimizing the brain stimulation parameters of the target subject to obtain the brain stimulation rule suitable for the target subject through the artificial intelligence algorithm, and generating individual-targeted brain stimulation for the target subject according to the brain stimulation rule, making the brain stimulation more scientific, effective, and accurate.

As a cloud server, the cloud platform uses the artificial intelligence algorithm to generate the multi-dimensional psychological big data. The data is obtained from two sources: existing medical knowledge and available data authorized by the target subject. The existing medical knowledge is obtained by analyzing existing medical research literature, public or commercially available medical cases through natural language processing and constructing a knowledge database. For example, the knowledge database may include possible illnesses corresponding to arrhythmia or low spirits of the target subject, symptoms, indicators and subdivided types of various illnesses, and treatment plans for each subdivided type of illnesses, which constitute diagnosis and treatment models of algorithm for various illnesses. Acquiring available data authorized by the target subject includes receiving data from sensors of the brain stimulation terminals. Each sensor performs real-time data collection with permission of the target subject, and the real-time data may include facial expression, voice, heartbeat, blood pressure, respiratory rate, skin conductivity, etc. of the target subject. By processing this data, diagnosis indicators related to illnesses may be obtained, such as subjective emotions (facial expression, emotional vocabulary in the voice, tone and voice speed, etc.), physiological emotions (skin conductivity, heart rate variability, blood pressure, heartbeat, etc.), degrees of mental fatigue (skin conductivity, facial expression, voice, etc.), attention, and auditory and visual hallucinations (speech feedback, used for schizophrenia diagnosis) of the target subject.

The cloud platform evaluates human psychological and mental state according to the above-mentioned data, comprehensively compares physiological indicator parameters from various sensors, the expression and voice of the current target subject, etc. through the artificial intelligence algorithm, and obtains relatively perfect and accurate composite indexes of human physiology and psychology, to deeply explore and analyze the current physiological and psychological state of the target subject. The cloud platform has advantages over the clinical single dimension. For example, when the target subject gives an "okay" answer, but actually shows a depressed expression and fluctuating psychological parameters, the cloud platform may analyze the current voice and expression from multiple dimensions and obtain the psychological data of the target subject, which is more scientific and accurate.

The cloud platform conducts big data and artificial intelligence processing and generates the multi-dimensional psychological big data for two goals. The first goal is to process illness-related indicators and diagnoses illnesses. Attention, current emotions and degrees of mental fatigue are calculated and related illnesses are diagnosed according to the existing medical knowledge, and calculation methods and detailed classification are adjusted dynamically according to the accumulated big data. For example, accelerated heartbeats and breaths may result from excitement or tension, which can be judged through the voice interaction content of the target subject. The accumulated physiological parameters of the target subject under different states, excitement or tension, are analyzed in detail and the previous emotional judgment model is learned and improved using machine learning and deep learning. On the other hand, in the process of interacting with the target subject, the type of illness is further clarified in conjunction with the answer and physiological parameters of the target subject. The big data of all target subjects are accumulated and comprehensively processed, to continuously adjust and improve the model and achieve more accurate indicator processing and illness diagnosis. The second goal is the adjustment treatment model. The initial model is existing treatment plans corresponding to illnesses in the knowledge database. The data feedback of the target subject is detected and collected in real time in the follow-up treatment process to evaluate the effectiveness of the current treatment and make optimized adjustment, which is made mainly through artificial intelligence algorithms. In order to ensure long-term health of the target subject, a reinforcement learning algorithm may be selected to formulate plans. The difference between the reinforcement learning algorithm and the traditional machine learning algorithm lies in that the reinforcement learning algorithm adjusts the model according to environmental feedback to achieve long-term benefits. For example, the goal of alphago playing Chinese chess is to win finally rather than take pieces of the opponent in the current or recent two steps, and likewise adjustment treatment algorithms are to enable the target subject to maintain long-term health rather than short-term physiological health or current needs. For the specific implementation of the reinforcement learning model, reference may be made to, but is not limited to, the following settings. The current physiological and mental state of the target subject is taken as "state", and the produced stimulation vectors are taken as "action". The stimulation vectors include stimulation type (visual, auditory, tactile, etc.) and stimulation modes such as frequencies, intensities, times, attributes (such as visual content, auditory song type, olfactory scent type, etc.). The feedback of the target subject is taken as rewards or punishments. Punishment scores are adjusted according to the degree of the current lower spirits and the increasing proportion of the originally high heart rates of the target subject, and reward scores are marked according to the degree of emotional improvement and healthier physiological parameters such as blood pressure. A weight is given to an adjustment strategy specified by the knowledge database through a series of feedback from the target subject. Other safe plans are correspondingly explored, the continuous feedback of the target subject after a series of stimulation treatments are record, and the treatment plan that can guarantee the highest score of the "state" of the target subject is selected. Due to the different habits and physiology of different target subjects, the reinforcement learning plan will make the stimulation treatment more individual, accurate and continuous, ensuring long-term medical health. Meanwhile, a more comprehensive and suitable treatment plan is developed through performing big data mining and analysis on all plans of the target targets.

Figure 2:
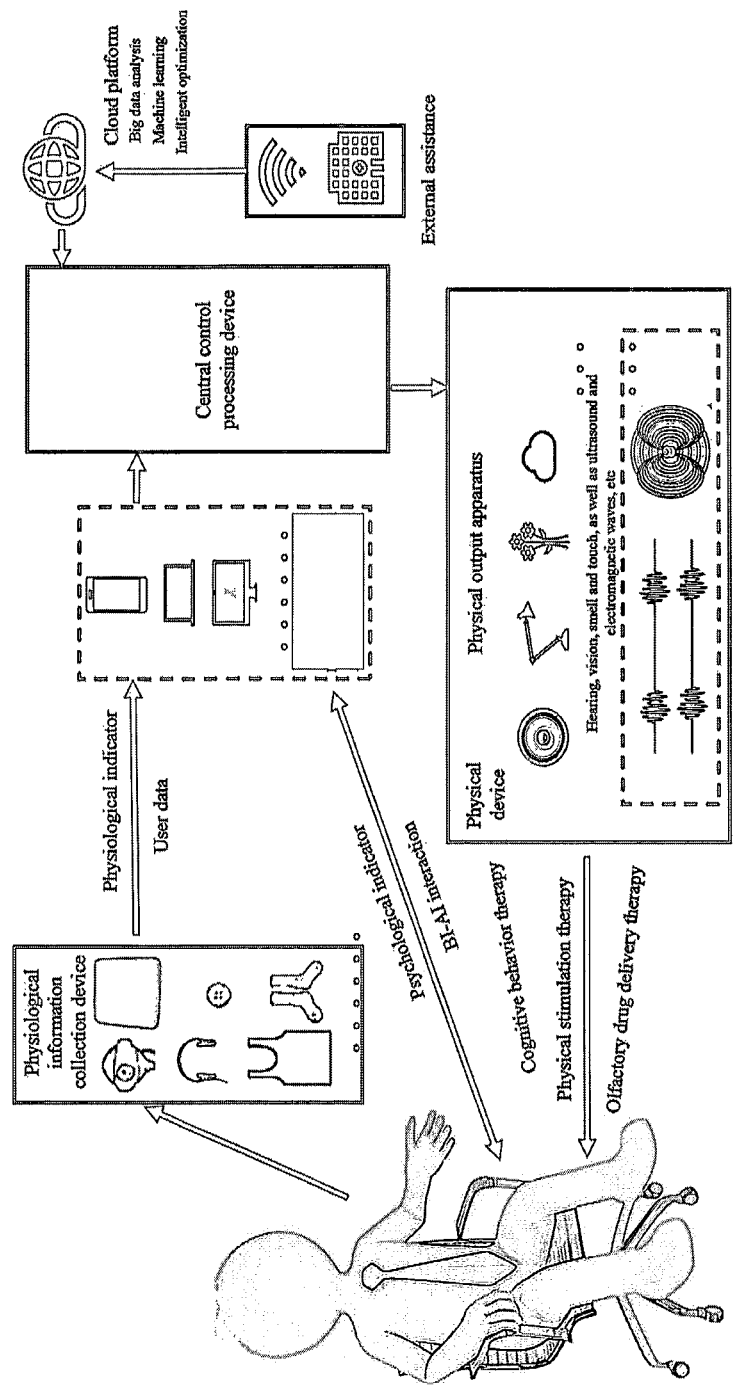
FIG. 2 is a block diagram illustrating a configuration of a brain stimulation terminal according to the embodiments of the present disclosure.

FIG. 2 is a block diagram illustrating a configuration of a brain stimulation terminal according to the embodiments of the present disclosure. Referring to FIG. 2, the brain stimulation terminal includes a physiological information collection device, a psychological communication interaction device, a central control processing device, and a physical output apparatus. The physiological information collection device is used for collecting the physiological data of the target subject. The psychological communication interaction device is used for human-machine interaction with the target subject through the NLP technology to obtain the psychological state evaluation parameters of the target subject. The central control processing device is used for controlling the physiological information collection device, the psychological communication interaction device and the physical output apparatus, analyzing the physiological data and psychological state evaluation parameters of the target subject based on the multi-dimensional psychological big data by using the artificial intelligence platform, measuring the mental state of the target subject, and obtaining brain stimulation parameters required for the target subject according to the mental state. The physical output apparatus operates according to the brain stimulation parameters to produce brain stimulation for the target subject.

On the basis of the above-mentioned technical solution, the physiological information collection device is further used for collecting facial expressions of the target subject through a camera, and sound features of the target subject through a microphone. The central control processing device is further used for analyzing the facial expressions and sound features of the target subject through the artificial intelligence algorithm and measuring the mental state of the target subject.

The physiological information collection device collects the main physiological indicator parameters of the human body, including heart rate, respiratory rate, blood pressure, pressure index, brain wave, attention value, a fatigue level, etc.; transmits data through wireless technologies such as Bluetooth, and is compatible with daily computers, notebooks and mobile phones. The physiological information collection device may be a fine and concealed electronic sensing device made of flexible materials, and an electronic micro element is packaged with soft and transparent materials with good biocompatibility such as polydimethylsiloxane (PDMS). Specifically, the physiological information collection device may be made into a skin-conductivity-sensitive sensor that is tightly integrated with a mobile phone case, a pressure-sensitive sensor placed in the chair cushion, and related sensors disposed on an inner surface of clothes, buttons or socks. The collected data is transmitted, through Bluetooth and other technologies, to and compatibly used by common intelligent apparatuses such as computers, notebooks and mobile phones, and used in conjunction with cameras and microphones of these apparatuses. Compared with existing electronic sensors and systems on the market, sensor elements have better affinity with the human body in addition to data collection accuracy, because the sensor elements are mainly made of polymer materials with good biocompatibility. In addition, the sensor elements are more compatible with ordinary computers or mobile phones, and the energy consumption is low. The system collects the physiological health data of the human body, including heart rate, blood pressure, respiratory rate, attention, degree of mental fatigue, etc., focuses on comprehensiveness and scientificity, and implements functions through two or more types of sensors.

The psychological communication interaction device achieves human-machine communications through the common natural language process (NLP) technology. The psychological communication interaction device interacts with the target subject through the natural language process technology in conjunction with the interaction capability of local intelligent apparatuses such as computers, notebooks and mobile phones, and acquires the psychological state evaluation parameters of the target subject with reference to the data related to clinical psychology.

The central control processing device constructs a medical knowledge database of brain diseases and psychology, analyzes, based on the multi-dimensional psychological big data, physiological state data such as the current expressions and physiological parameters of the target subject collected in real time, measures a more accurate mental state of the target subject, and measures the brain stimulation parameters required for the target subject. The central control processing device achieves main functions of the artificial intelligence including the medical knowledge database of brain diseases and psychology, classifying individual physiological and psychological big data, real-time organizing and optimizing multi-dimensional data, and screening output programs, with the aid of the computing power of local apparatuses (such as computers, notebooks and mobile phones) and the big data processing capability of the cloud platform. The central control processing device and the cloud platform work synchronously and share data in real time. For example, when the target subject interacts with the brain stimulation system by voice, the central control processing device analyzes the current target subject's expression, cardiac rhythm, blood pressure, and other parameters, measures the current mental state of the target subject, figures out by comprehensive analysis whether the request or demand of the target subject is reasonable in the current state (for example, if it is very late night and the physiological parameters of the target subject exhaustion, but the target subject still expresses the desire of listening to rock songs by voice), and recommends the fond emotional adjustment of the target subject (telling the target subject that it is time to go asleep at this time and excitement songs are not very suitable in the current state and suggesting light songs in the favorite list for the target subject), so as to achieve all-round, scientific, healthy, good brain stimulation adjustment required for the target subject.

The physical output apparatus mainly conducts effective intervention on the brain neural circuit related to emotional and mental regulation through non-invasive and multi-sensory brain stimulation techniques. The stimuli mainly include sensory stimuli in vision, hearing, smell, and touch, as well as cerebral cortex stimuli in electromagnetic waves and deep brain stimuli in ultrasound. The brain stimulation terminal may provide three intervention methods, including a physical stimulation therapy, an olfactory drug delivery therapy and a cognitive behavior therapy. These therapies can provide effective prevention and intervention for mental health problems and brain diseases; and at least provide early prediction, timely prevention and professional intervention for patients with severe depression, autism, and schizophrenia. The physical output apparatus has the multi-sensory non-invasive brain stimulation function, and has more scientific and accurate stimulation effects in conjunction with the artificial intelligence algorithm of the central control processing device, finds more accurate individual-targeted stimulation parameters and programs through the algorithm optimization, and finally obtains, through intelligent memory and loop optimization, the best parameters suitable for personal adjustment. The physical output apparatus generates the brain stimulation parameters more intelligently, including the output of the program of the physical stimulation therapy, the raw materials screening of the olfactory drug delivery therapy and the flexible application of the cognitive behavior therapy. The physical output apparatus includes any one or more of the following devices: a light source device, a sound device, a massage device, a incense device, a ultrasonic device, and an electromagnetic wave device. The light source device, sound device, and massage device are used for conducting sensory physical stimulation generated by corresponding stimulation programs on the target subject. The ultrasonic device and electromagnetic wave device are used for conducting professional medical brain stimulation on the target subject to achieve medical treatment effects. As regards the output of the program of the physical stimulation therapy, combination plans of multiple sensory stimuli are provided, including vision, hearing and touch, and then the corresponding stimulation programs are selected according to the calculation results of the physiological and psychological detection data. Each stimulation program includes multiple sensory stimuli. Each stimulus includes a specific frequency, an intensity, a time parameter, etc. More accurate choices of these parameters are made through artificial intelligence calculations. The incense device is used for spreading molecules of chemical gas via the air into the olfactory organ of the target subject to achieve the olfactory drug delivery intervention or treatment effect. The olfactory drug delivery therapy may be implemented by a fumigation facility in a closable hardware environment. In this environment, the molecules of chemical gas are transferred into the olfactory organ of the human body via the air and then enter, through the smell, the limbic system of the brain responsible for emotional cognition. The used chemical drugs are mainly flavor materials and Chinese medicine ingredients that are recognized as safe and effective and FDA-approved western medicine ingredients. Raw materials are made into nanoscale granules, packaged in the vicinity of the incense device, are automatically screened for use by the hardware apparatuses through artificial intelligence algorithms. The psychological communication interaction device is not only used for human-machine interaction with the target subject, but also for the cognitive behavior therapy of the target subject. The human-machine interaction includes written communication, voice conversation, game interaction, picture playback and/or video playback. In the cognitive behavioral therapy, by using the natural language process (NLP) technology, the human-machine interaction is implemented including program selection, typing and chatting, and human-machine dialogue, the psychological and mental state is evaluated in conjunction with the table of clinical diagnostic criteria, and the cognitive behavior therapy is flexibly implemented in humorous human-machine interaction ways, including jokes, games, cartoons and videos, to achieve the purpose of regulating emotions and mental states.

With the technical solution according to the embodiments, accurate prediction, prevention, and intervention are provided for physical and mental health problems in an intelligent, individual-targeted, scientific and comprehensive manner. The technical solution includes a mental health detection technology and provides individual-targeted, comprehensive, and scientific prevention and intervention after individual detection, and the prevention and intervention include the cognitive behavioral therapy, the physical stimulation therapy, and the olfactory drug delivery therapy. In addition, the technical solution has certain effects on multiple brain diseases in conjunction with big data and artificial intelligence, and particularly provides at least early prediction, timely prevention and professional intervention for depression, autism and schizophrenia. Besides the cognitive behavioral therapy through the human-machine interaction system, more comprehensive and accurate prevention and intervention measures are implemented through other technologies, including a sophisticated physiological and psychological monitoring system, a non-invasive multi-sensory brain stimulation technology, and a seizure emergency alert function. Therefore, the solution can not only help people maintain mental health and regulate negative emotions, but also help to treat the most serious mental illnesses, including depression, autism and schizophrenia.

On the basis of the above-mentioned technical solution, the brain stimulation terminal further includes a power supply device, which is used for supplying power to the brain stimulation terminal. The power supply device includes any one or more of the following devices: a primary battery, a secondary battery, a radio frequency power supply battery, and a biological fuel battery.

Figure 3:
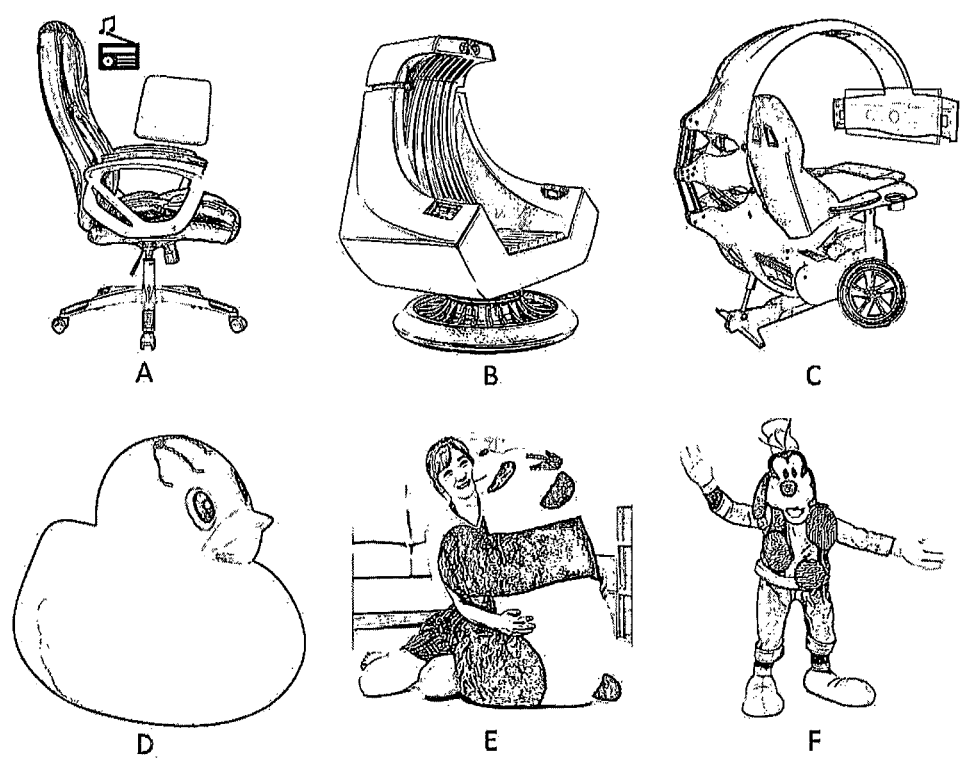
FIG. 3 is a diagram illustrating exemplary products of a brain stimulation terminal according to the embodiments of the present disclosure.

FIG. 3 illustrates specific exemplary products of the brain stimulation terminal according to embodiments of the present disclosure. Referring to FIG. 3, A is an accessory of an intelligent office chair suitable for the public, including an App software. The App software can preliminarily detect a user's moods and health states through the face recognition and fingerprint scanning functions of a computer and a mobile phone. B is the open Chair product with the non-invasive multi-sensory brain stimulation function. C is a product with new type scooter Auto-chair with office functions, which provides a complete non-invasive multi-sensory brain stimulation function through a close system, is suitable for outdoor office and might have an automatic driving function. D is a product like an intelligent yellow duck suitable for autistic children, and has the complete monitoring, interaction and brain stimulation functions. E is a product like an intelligent panda for patients with depression, and has the complete monitoring, interaction and brain stimulation functions. F is a product like an intelligent Goofy nurse suitable for patients with schizophrenia, and has the complete monitoring, interaction and brain stimulation functions.

The brain stimulation terminal includes two types: a universal type for the ordinary people, and an illness type for those patients with brain diseases. Universal products may be App software directly used in mobile phones and computers, as well as some hardware apparatuses placed next to mobile phones and computers, such as smart cushions and smart office chairs (see A, B, and C in FIG. 3). The APP software collects basic physiological parameters of the human body including heartbeat, respiration and blood pressure through a galvanic skin sensor that may be tightly attached to the mobile phone cover, a pressure-sensitive sensor placed in the chair cushion, and collects the facial expressions and/or the sound features of the target subject through cameras and/or microphones of computers and mobile phones, so as to collect more accurately the comprehensive physiological data of the human body. On the other hand, the human-machine interaction function of the App software may obtain the user's psychological evaluation parameters by way of typing communication and voice conversation. Artificial intelligence algorithms are employed in processing and analyzing the physiological and psychological big data to obtain the user's mental state, and visual and auditory sensory stimuli are provided by computers or mobile phones for adjustment. In addition, in conjunction with the smart chair, multi-sensory comprehensive adjustment in touch, smell, and ultrasound and electromagnetic waves can be achieved. Illness-type products, which focus on caring for, monitoring, and helping patients with brain diseases, appear as pets with good affinity (see D, E and F in FIG. 3), and has the complete functions of the above-mentioned three systems. Besides the above-mentioned forms, sensors responsible for collecting the physiological data of the human body exist in a more subtle form, such as being hidden inside clothes, buttons or socks. The products interact daily with the user in a friendly, funny, caring and tacit way with the human-machine interaction function, and get together with the user all day like real pets. The comprehensive physiological and psychological parameters obtained through accumulated big data are processed, organized and optimized using artificial intelligence, and then patients are provided with an optimal set of adjustment programs. Beneficial intervention and adjustment are conducted on patients with mental illnesses through the non-invasive multi-sensory neural-circuit stimulation. The products issue a pre-warning and provide effective prevention and timely intervention in the event of a seizure or deterioration of an illness. When the patient is not in a wellbeing state, the mental health state of the patient can be adjusted systematically, scientifically and intelligently through the cognitive behavioral therapy, the physical stimulation therapy and the olfactory drug delivery therapy.

Figure 4:
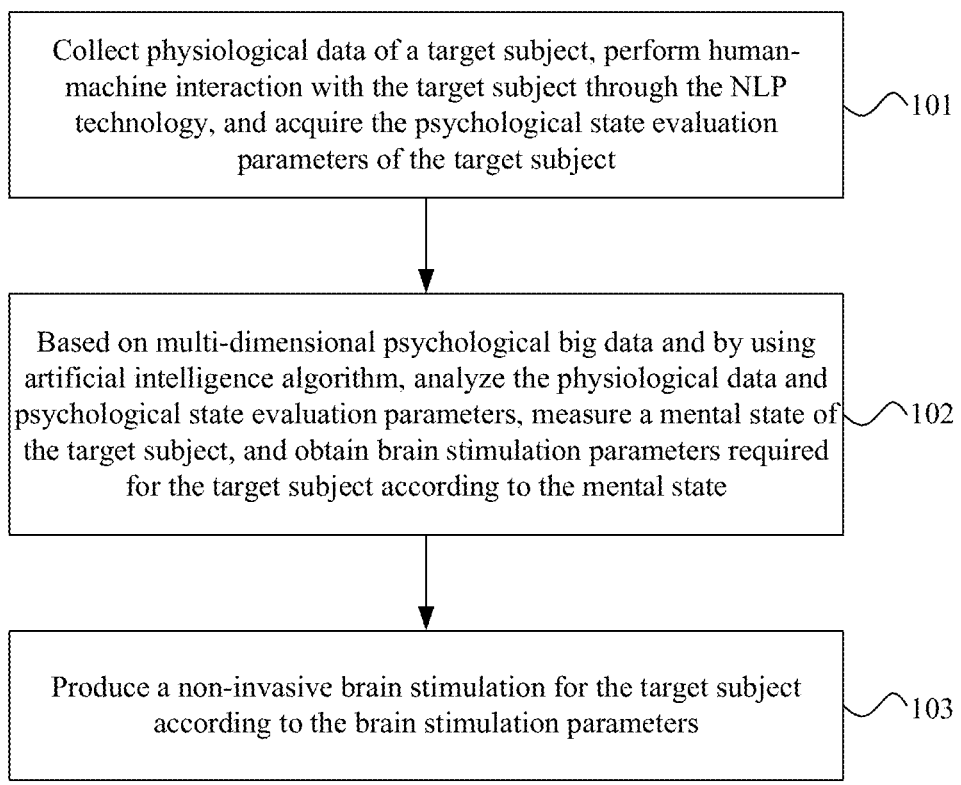
FIG. 4 is a flowchart of a brain stimulation method based on artificial intelligence according to embodiments of the present disclosure.

FIG. 4 is a flowchart of a brain stimulation method based on artificial intelligence according to the embodiments of the present disclosure. The method includes the steps described below.

In step 101, the physiological data of the target subject is collected and the human-machine interaction with the target subject is performed through the NLP technology, and the psychological state evaluation parameters of the target subject are acquired.

In step 102, the physiological data and psychological state evaluation parameters are analyzed based on multi-dimensional psychological big data and by using artificial intelligence algorithm, the mental state of the target subject is measured, and the brain stimulation parameters required for the target subject are obtained according to the mental state.

In step 103, the corresponding non-invasive brain stimulation for the target subject are generated according to the brain stimulation parameters.

On the basis of the above-mentioned technical solution, the method further includes the following steps. The multi-dimensional psychological big data is generated by learning a lot of physiological data and psychological state evaluation parameters and combining the established models of algorithm for disease diagnosis through the artificial intelligence algorithm. The multi-dimensional psychological big data is cyclically calculated and optimized through the artificial intelligence algorithm. The possibility of a mental illness of the target subject is predicted according to the mental state and the corresponding pre-warnings and/or adjustment and intervention are made. The brain stimulation parameters of the target subject are comprehensively recorded, and are studied to obtain the brain stimulation rule suitable for the target subject through the artificial intelligence algorithm. More scientific, effective and accurate brain stimulation is generated for the target subject according to the brain stimulation rule. Facial expressions of the target subject are collected through a camera, and sound features of the target subject are collected through a microphone. The facial expressions and sound features of the target subject are analyzed through the artificial intelligence algorithm and the mental state of the target subject is measured.

Figure 5:
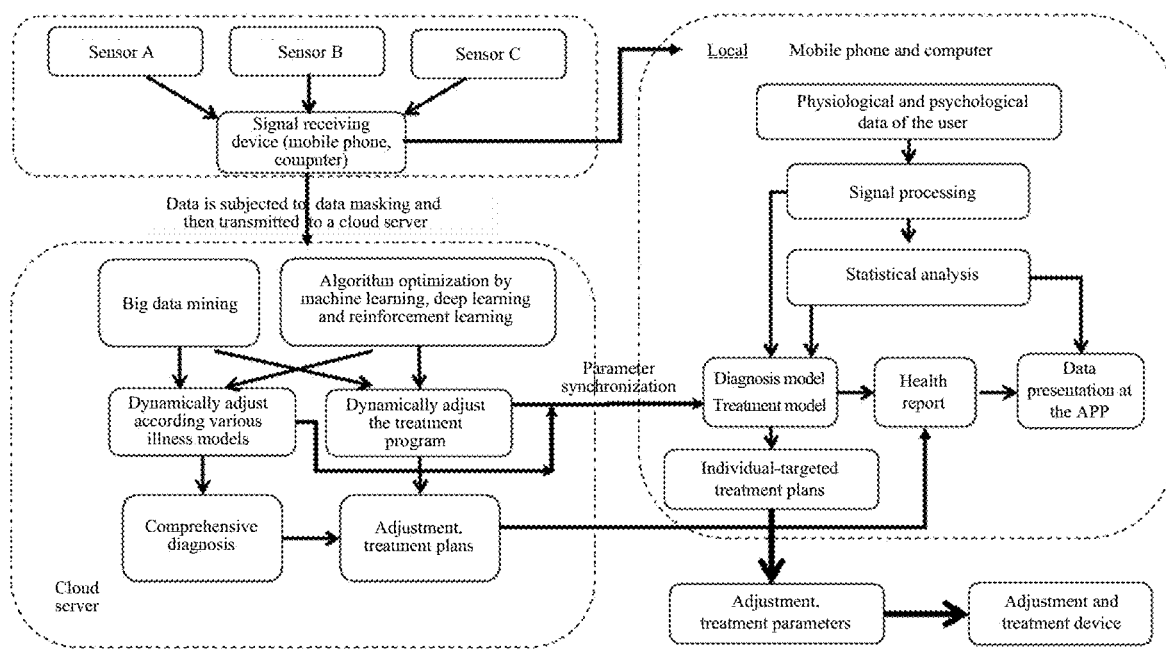
FIGS. 5 and 6 are flowcharts of a brain stimulation method based on artificial intelligence according to the embodiments of the present disclosure.
Figure 6:
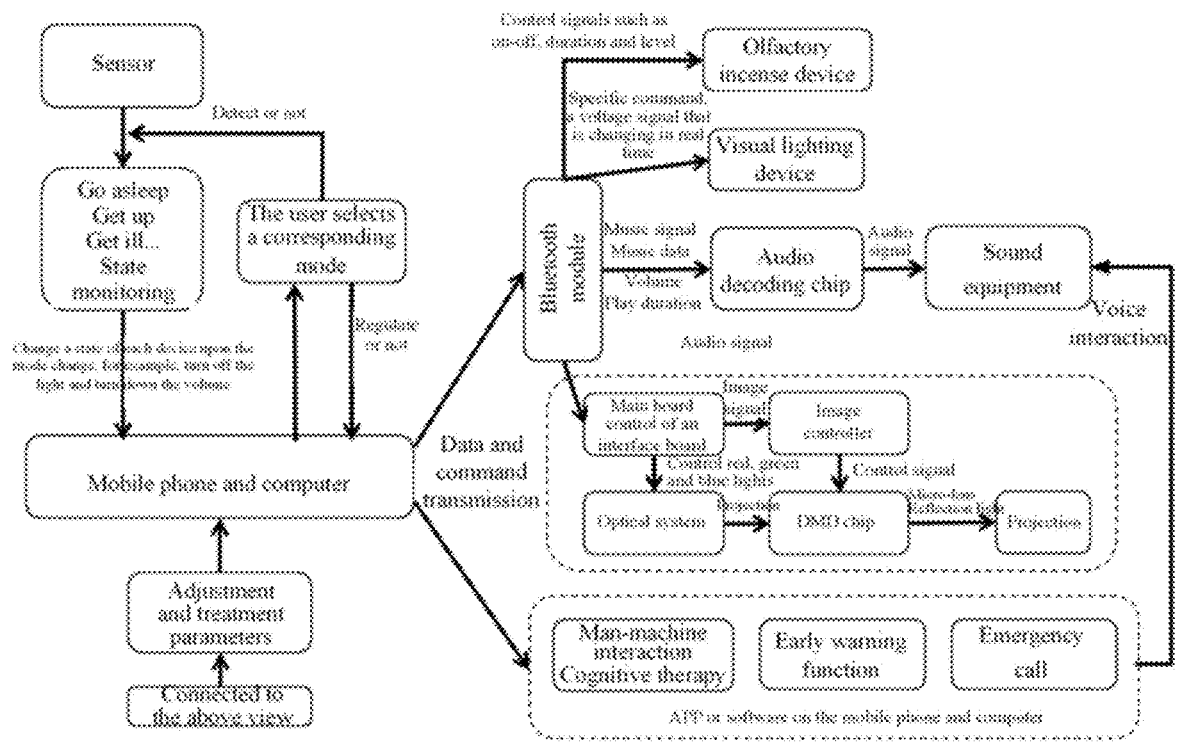

FIGS. 5 and 6 are flowcharts of a brain stimulation method based on artificial intelligence according to the embodiments of the present disclosure. The process is divided into a local part and a cloud part. As shown in FIG. 5, the data of the target subject collected by a plurality of sensors is transmitted to the mobile phone or the computer. On the one hand, a local system (that is, the mobile phone and the computer) performs calculation and processing. On the other hand, a cloud server performs artificial intelligence algorithm processing of big data. The local system analyzes, integrates and optimizes the data according to the existing intelligent programs and algorithms, produces individual-targeted health reports and intervention treatment plans and provides optimal adjustment programs. The cloud server mainly collects the integrated big data of the physiological and psychological data which has been subjected to data masking, further performs data mining on the individual health big data, and continuously optimizes artificial intelligence algorithms to improve the intelligence and accuracy of the system. In addition, as shown in FIG. 6, after the intelligent system generates the brain stimulation parameters, each stimulation device receives a program command and performs stimulation. The target subject firstly independently selects main program modes through Apps on the mobile phone or the computer, and then the parameters generated by artificial intelligence is further optimized and provided in conjunction with the selected mode. Finally, the parameters are provided to various physical apparatuses, including optical systems, sound facilities, incense devices, human-machine interaction systems, etc. After the stimulation, the sensor system simultaneously collects and gathers feedback data.

If target subject may feel uncomfortable or anxious about brain stimulation, they will be reassured that stimulation is optional; and also that data from target subject will be protected in the whole AI-based system in terms of that privacy safety, including use of anonymous IDs, password protected personal identifying information, encrypted storage of the personal data at cloud database, and limiting the use of the database by persons responsible for performing data analyses and algorithm manipulation.

Figure 7A:
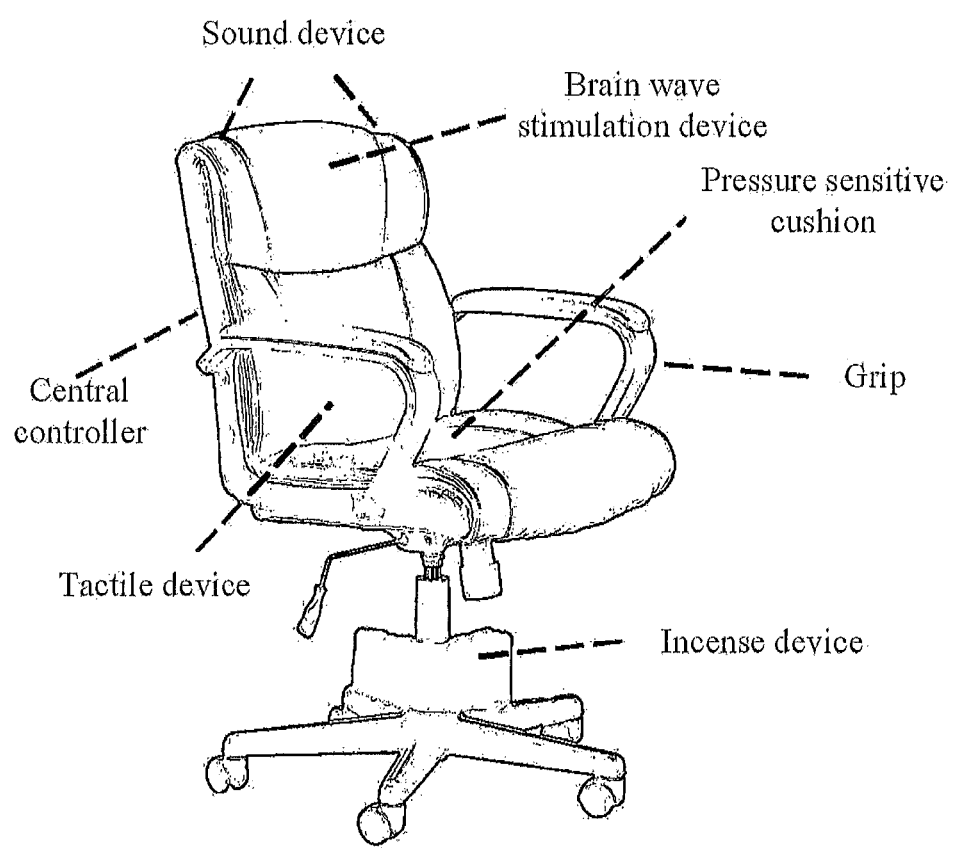
FIGS. 7A and 7B are diagrams illustrating exemplary products of a brain stimulation terminal according to the embodiments of the present disclosure.
Figure 7B:
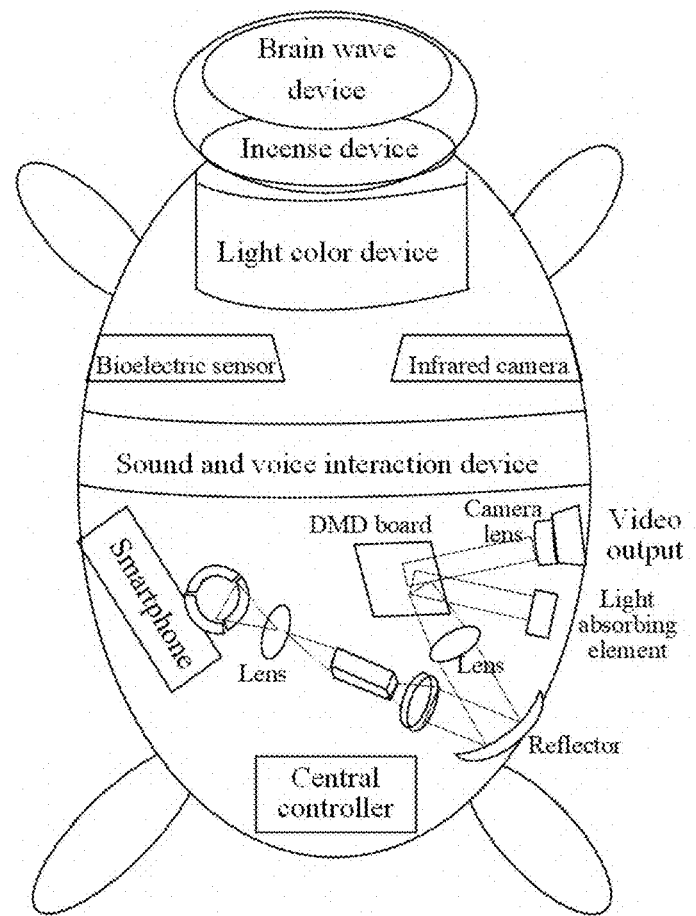

FIGS. 7A and 7B illustrate exemplary products of a brain stimulation terminal according to the embodiments of the present disclosure. FIG. 7A illustrates one form of the supporting hardware of the brain stimulation system, a smart chair. This hardware is provided with various sensory stimulation devices, including a sound device, a brain wave stimulation device, a grip, an incense device and a tactile device. In addition, further provided are a pressure sensitive cushion at the seat and a central controller at the back of the chair. FIG. 7B illustrates another form of the supporting hardware of the brain stimulation system, a smart robotic pet. This hardware is provided with various sensory stimulation devices, including a brain wave stimulation device, an incense device, a sound and voice interaction device and a video output apparatus. In addition, further provided are an infrared camera, a bioelectric sensitive sensor, a central controller and a smartphone. The smartphone has data transmission and communication functions and is capable to transmit the big data of the human body to a guardian at another end and automatically contact the guardian if necessary.

Figure 8:
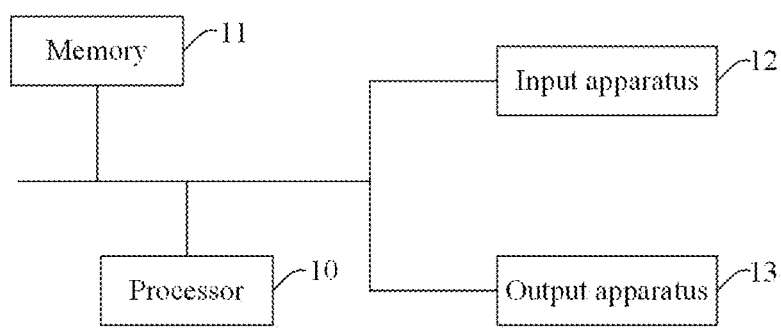
FIG. 8 is a block diagram illustrating a configuration of an apparatus according to the embodiments of the present disclosure.

FIG. 8 is a structural view of an apparatus according to the embodiments of the present disclosure. As shown in FIG. 8, the apparatus includes a processor 10, a memory 11, an input apparatus 12 and an output apparatus 13. One or more processors 10 may be disposed in the apparatus, and one processor 10 is taken as an example in FIG. 8. The processor 10, the memory 11, the input apparatus 12 and the output apparatus 13 in the apparatus may be connected by a bus or by other manners. Connection by a bus is used as an example in FIG. 8.

The memory 11 is used as a computer-readable storage medium for storing software programs, computer-executable programs and modules, such as program instructions/modules corresponding to the brain stimulation method based on artificial intelligence according to the embodiments of the present disclosure. The processor 10 executes various function applications and data processing of the apparatus, that is, implements the above-mentioned brain stimulation method based on artificial intelligence, by executing software programs, instructions and modules stored in the memory 11.

The memory 11 may mainly include a program storage area and a data storage area. The program storage area may store an operating system and at least one application required for functions. The data storage area may store data and the like created according to the use of the terminal. Furthermore, the memory 11 may include a high speed random access memory, and may also include a nonvolatile memory such as at least one disk memory, a flash memory or another nonvolatile solid-state memory. In some examples, the memory 11 may further include memories located remotely relative to the processor 10 and these remote memories may be connected to the apparatus via networks. Examples of such networks include, but are not limited to, the Internet, intranets, local area networks, mobile communication networks, and combinations thereof.

The input apparatus 12 may be used for receiving the input numerical or character information and for generating the key signal input related to the target subject settings and function control of the apparatus. The output apparatus 13 may include a display apparatus such as a display screen.

A storage medium storing executable instructions is provided according to the embodiments of the present disclosure. The executable instructions are configured to perform related operations in the brain stimulation method based on artificial intelligence according to any embodiment of the present disclosure.

Through the above description of the embodiments, it is clear to those skilled in the art that the embodiments of the present disclosure may be accomplished through software plus necessary universal hardware or through hardware, but in many cases, the former implementation is preferred. Based on such understandings, the essential technical solutions or the contribution to the related art of the embodiments of the present disclosure may be embodied in the form of a software product in conjunction with related supporting hardware, and the computer software product may be stored in a computer-readable storage medium, such as a floppy disk, a read-only memory (ROM), a random access memory (RAM), a flash memory, a hard disk, or an optical disk, etc., and includes several instructions for making a computer apparatus (which may be a personal computer, a server or a network apparatus, etc.) perform the method according to any one of the embodiments of the present disclosure.

It should be noted that the above are only exemplary embodiments of the present disclosure and the applied technical principles. Those skilled in the art will understand that the embodiments of the present disclosure are not limited to the specific embodiments described herein, and those skilled in the art can make various apparent changes, modifications and substitutions without departing from the scope of the embodiments of the present disclosure. Therefore, despite the detailed description of the above embodiments, the embodiments of the present disclosure are not limited to the above embodiments, and may include other equivalent embodiments without departing from the concept of the embodiments of the present disclosure. The scope of the embodiments of the present disclosure is determined by the scope of the appended claims.

What is claimed is:

1. A brain stimulation system comprising: a plurality of brain stimulation terminals and a cloud platform in communication connection with the plurality of brain stimulation terminals, wherein the cloud platform is configured to: generate multi-dimensional psychosomatic big data using physiological data and psychological state evaluation parameters gotten from the plurality of brain stimulation terminals and established models of algorithm for brain disease diagnosis or evaluation;

wherein each of the plurality of brain stimulation terminals comprises a physiological information collection device, a psychological communication interaction device, a central control processing device and a physical output apparatus, wherein the physiological information collection device is configured to collect physiological data of a target subject;

the psychological communication interaction device is configured to perform human-machine interaction with the target subject through a natural language processing technology and acquire the psychological state evaluation parameters of the target subject;

the central control processing device is configured to control the physiological information collection device, the psychological communication interaction device and the physical output apparatus, to measure a mental state of the target subject corresponding to the physiological data and the psychological state evaluation parameters of the target subject based on the multi-dimensional psychosomatic big data and a medical knowledge database, and to obtain the brain stimulation parameters required for the target subject according to the mental state; and the physical output apparatus is configured to operate according to the brain stimulation parameters to produce the brain stimulation for the target subject;

wherein the established models of algorithm for brain disease diagnosis or evaluation is constituted by the following manners: the cloud platform constructs the medical knowledge database according to preset medical knowledge; and the cloud platform constitutes the established models of algorithm for brain disease diagnosis or evaluation according to the medical knowledge database; wherein the medical knowledge database comprises at least one of the followings: a corresponding relationship between the physiological data and various illnesses, a corresponding relationship between the psychological state evaluation parameters and the various illnesses, a corresponding relationship between the physiological data and the psychological state evaluation parameters and various diseases, symptoms of the various illnesses, indicators of the various illnesses, subdivided types of the various illnesses, treatment plans for each of the subdivided types of the various illnesses.

2. The system according to claim 1, wherein the cloud platform is further configured to perform loop calculation on the multi-dimensional psychosomatic big data to optimize the multi-dimensional psychosomatic big data.

3. The system according to claim 1, wherein the each of the plurality of brain stimulation terminals is further configured to predict a possibility of a mental illness of the target subject according to the mental state and make at least one of the following corresponding operations: pre-warnings, adjustment or intervention.

4. The system according to claim 1, wherein the each of the plurality of brain stimulation terminals is further configured to comprehensively record the big data of the target subject, optimize the brain stimulation parameters of the target subject to obtain a brain stimulation rule suitable for the target subject, and produce individual-targeted brain stimulation for the target subject according to the brain stimulation rule.

5. The system according to claim 1, wherein the physiological information collection device is configured to collect the physiological data by sensors, wherein the sensors comprise a galvanic skin response collection device, a brain wave collection device and a photoelectric plethysmograph device.

6. The system according to claim 5, wherein the physiological information collection device is further configured to collect facial expressions of the target subject through a camera and collect sound features of the target subject through a microphone; and the central control processing device is further configured to measure the mental state of the target subject corresponding to the facial expressions and the sound features of the target subject based on the multi-dimensional psychosomatic big data and the medical knowledge database.

7. The system according to claim 1, wherein the physical output apparatus comprises one or more of the following devices: a light source device, a sound device, a massage device, an odorous device, an ultrasonic device and an electromagnetic wave device.

8. The system according to claim 7, wherein the light source device, the sound device and the massage device are configured to provide physical sensory stimulation for performing a stimulation program on the target subject.

9. The system according to claim 7, wherein the odorous device is configured to spread chemical molecules via air into an olfactory organ of the target subject to achieve an olfactory drug delivery intervention or treatment effect.

10. The system according to claim 7, wherein the ultrasonic device and the electromagnetic wave device are configured to perform a professional brain stimulation on the target subject to achieve an intervention or treatment effect in a specific brain region.

11. The system according to claim 1, wherein the psychological communication interaction device is further configured to perform a cognitive behavior therapy on the target subject through the human-machine interaction, wherein the human-machine interaction comprises written communication, voice conversation, game interaction, and imagery intervention with images or videos.

12. The system according to claim 1, wherein the each of the plurality of brain stimulation terminals further comprises a power supply device, wherein the power supply device is configured to supply power to the each of the plurality of brain stimulation terminals, and the power supply device comprises one or more of the following devices: a primary battery, a secondary battery, a radio frequency power supply battery, and a biofuel battery.

13. The system according to claim 1, wherein the physiological data comprises a heart rate, a respiratory rate, a blood pressure, skin conductivity and a brain wave, and the psychological state evaluation parameters comprise a pressure index, an attention value and a fatigue level.

14. A brain stimulation method, applied to a brain stimulation system, wherein the brain stimulation system comprises a plurality of brain stimulation terminals and a cloud platform in communication connection with the plurality of brain stimulation terminals, each of the plurality of brain stimulation terminals comprises a physiological information collection device, a psychological communication interaction device, a central control processing device and a physical output apparatus; the method comprises:

generating, by the cloud platform. multi-dimensional psychosomatic big data using physiological data and psychological state evaluation parameters gotten from the plurality of brain stimulation terminals and established models of algorithm for brain disease diagnosis or evaluation;

collecting, by the physiological information collection device, physiological data of a target subject;

performing, by the psychological communication interaction device, human-machine interaction with the target subject through a natural language processing technology and acquiring, by the psychological communication interaction device, the psychological state evaluation parameters of the target subject;

controlling, by the central control processing device, the physiological information collection device, the psychological communication interaction device and the physical output apparatus, measuring, by the central control processing device, a mental state of the target subject corresponding to the physiological data and the psychological state evaluation parameters of the target subject based on the multi-dimensional psychosomatic big data and a medical knowledge database, and obtaining, by the central control processing device, the brain stimulation parameters required for the target subject according to the mental state; and operating, by the physical output apparatus, according to the brain stimulation parameters to produce the brain stimulation for the target subject;

wherein the established models of algorithm for brain disease diagnosis or evaluation is constituted by the following manners: the cloud platform constructs the medical knowledge database according to preset medical knowledge; and the cloud platform constitutes the established models of algorithm for brain disease diagnosis or evaluation according to the medical knowledge database; wherein the medical knowledge database comprises at least one of the followings: a corresponding relationship between the physiological data and various illnesses, a corresponding relationship between the psychological state evaluation parameters and the various illnesses, a corresponding relationship between the physiological data and the psychological state evaluation parameters and various diseases, symptoms of the various illnesses, indicators of the various illnesses, subdivided types of the various illnesses, treatment plans for each of the subdivided types of the various illnesses.

15. The method according to claim 14, further comprising: performing, by the cloud platform, loop calculation on the multi-dimensional psychosomatic big data to optimize the multi-dimensional psychosomatic big data.

16. The method according to claim 14, further comprising: predicting, by the each of the plurality of brain stimulation terminal, a possibility of a mental illness of the target subject according to the mental state and making at least one of the following corresponding operations: pre-warnings, adjustment or intervention.

17. The method according to claim 14, further comprising: comprehensively recording. by the each of the plurality of brain stimulation terminal, the big data of the target subject, optimizing, by the each of the plurality of brain stimulation terminal, the brain stimulation parameters of the target subject to obtain a brain stimulation rule suitable for the target subject, and producing, by the each of the plurality of brain stimulation terminal, individual-targeted brain stimulation for the target subject according to the brain stimulation rule.

18. The method according to claim 14, further comprising: collecting, by the physiological information collection device, facial expressions of the target subject through a camera and collecting sound features of the target subject through a microphone, analyzing the facial expressions and the sound features of the target subject and measuring the mental state of the target subject.

19. A device, comprising a memory, a processor, and programs stored in the memory and executable by the processor, wherein, execution of the programs by the processor causes the processor to implement the brain stimulation method according to claim 14.

20. The device according to claim 19, comprising any one of the following: a smartphone, a computer, a smart robot pet and a smart medical instrument.

21. A non-transitory storage medium storing executable instructions that when executed by a processor, causes the processor to implement the brain stimulation method according to claim 14.

* * * * *